(12) United States Patent
Brown, Jr. et al.

(10) Patent No.: US 9,642,340 B2
(45) Date of Patent: May 9, 2017

(54) REMOTE PET MONITORING SYSTEMS AND METHODS

(71) Applicant: Elwha LLC, Bellevue, WA (US)

(72) Inventors: Allen L. Brown, Jr., Bellevue, WA (US); Douglas C. Burger, Bellevue, WA (US); Alistair K. Chan, Bainbridge Island, WA (US); Eric Horvitz, Kirkland, WA (US); Roderick A. Hyde, Redmond, WA (US); Edward K.Y. Jung, Bellevue, WA (US); Chris D. Karkanias, Sammamish, WA (US); John L. Manferdelli, San Francisco, CA (US); Craig J. Mundie, Seattle, WA (US); Nathan P. Myhrvold, Medina, WA (US); Barney Pell, San Francisco, CA (US); Clarence T. Tegreene, Mercer Island, WA (US); Charles Whitmer, North Bend, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 239 days.

(21) Appl. No.: 14/333,273

(22) Filed: Jul. 16, 2014

(65) Prior Publication Data

US 2016/0015005 A1 Jan. 21, 2016

(51) Int. Cl.
*G08B 23/00* (2006.01)
*A01K 29/00* (2006.01)

(52) U.S. Cl.
CPC ................. *A01K 29/005* (2013.01)

(58) Field of Classification Search
CPC ..... G11B 27/036; G11B 27/005; G11B 27/34; H04W 4/005; H04W 52/0206; H04W 60/00; H04W 76/021; H04W 76/023; H04W 76/048; H04W 84/20; H04W 8/26; A01K 29/005; G06F 19/322; G06F 19/3406; G08B 13/01
USPC ..... 340/573.3, 573.4, 539.1, 539.11, 539.13, 340/6.1, 8.1, 539.16, 568.1, 572.1, 539.32
See application file for complete search history.

(56) References Cited

U.S. PATENT DOCUMENTS

| | | | |
|---|---|---|---|
| 5,207,179 A | 5/1993 | Arthur et al. | |
| 5,927,233 A | 7/1999 | Mainini et al. | |
| 6,043,748 A * | 3/2000 | Touchton | A01K 15/02 119/721 |
| 6,072,392 A | 6/2000 | Henderson et al. | |
| 6,375,612 B1 | 4/2002 | Guichon et al. | |
| 6,693,585 B1 | 2/2004 | MacLeod | |
| 6,825,768 B2 | 11/2004 | Stapelfeld et al. | |

(Continued)

*Primary Examiner* — Daniel Previl
(74) *Attorney, Agent, or Firm* — Foley & Lardner LLP

(57) ABSTRACT

A system for monitoring a pet includes a base station and a first monitoring device configured to capture first data relating to a first monitored area and to transmit the first data to the base station. The system further includes a second monitoring device configured to capture second data relating to a second monitored area and to transmit the second data to the base station, wherein the first monitored area and the second monitored area are adjacent. The base station is configured to determine a location of the pet as being in at least one of the first monitored area and the second monitored area. The base station is configured to determine a status of the pet based on at least one of the first and second data.

30 Claims, 8 Drawing Sheets

(56) References Cited

U.S. PATENT DOCUMENTS

| | | |
|---|---|---|
| 2002/0152969 A1 | 10/2002 | Grigsby et al. |
| 2002/0169583 A1 | 11/2002 | Gutta et al. |
| 2003/0034893 A1 | 2/2003 | Stapelfeld et al. |
| 2003/0058111 A1* | 3/2003 | Lee .................... G06K 9/00342 340/573.1 |
| 2003/0190076 A1 | 10/2003 | DeLean |
| 2005/0083204 A1 | 4/2005 | Stewart |
| 2005/0159863 A1 | 7/2005 | Howard et al. |
| 2005/0284412 A1 | 12/2005 | Kroll |
| 2006/0011146 A1* | 1/2006 | Kates .................... A01K 15/021 119/719 |
| 2007/0068017 A1 | 3/2007 | Tamura et al. |
| 2007/0107673 A1 | 5/2007 | Langer et al. |
| 2008/0072841 A1 | 3/2008 | So |
| 2008/0134988 A1 | 6/2008 | Dorman |
| 2008/0272920 A1 | 11/2008 | Brown |
| 2008/0282988 A1* | 11/2008 | Bloksberg ................ A01K 5/02 119/51.02 |
| 2009/0021585 A1* | 1/2009 | Ko .................... G08B 13/19656 348/184 |
| 2009/0090305 A1* | 4/2009 | Cheok .................... A01K 15/02 119/707 |
| 2009/0106044 A1 | 4/2009 | Schweisguth et al. |
| 2009/0118869 A1 | 5/2009 | Cauchy et al. |
| 2009/0194037 A1 | 8/2009 | So |
| 2009/0215533 A1 | 8/2009 | Zalewski et al. |
| 2009/0223463 A1 | 9/2009 | Chem |
| 2011/0256515 A1* | 10/2011 | Miller ...................... G09B 9/00 434/219 |
| 2013/0220233 A1* | 8/2013 | Lampman .............. A01K 3/002 119/712 |
| 2014/0184749 A1* | 7/2014 | Hilliges ................. G01S 17/89 348/47 |
| 2014/0267720 A1* | 9/2014 | Miller .................. A01K 15/025 348/143 |

* cited by examiner

REMOTE PET MONITORING SYSTEMS AND METHODS

BACKGROUND

Pets are often left alone at home for hours at a time as owners spend the time from home. While at home, a pet may be involved in situations that require attention from the owner. For example, a pet that is left at home may experience a health problem that requires immediate attention. In these situations, the pet's health problem may go unnoticed for many hours until the pet's owner returns home. As another example, a pet may enter a restricted area of the home (e.g., a bedroom) or damage furniture in the home (e.g., tear apart a pillow). The pet's actions may go unnoticed because the owner is away from home. Still further, an owner may miss a pet and desire to view the pet and interact with the pet while away from home.

SUMMARY

One embodiment relates to a system for monitoring a pet. The system includes a base station and a first monitoring device configured to capture first data relating to a first monitored area and to transmit the first data to the base station. The system further includes a second monitoring device configured to capture second data relating to a second monitored area and to transmit the second data to the base station, wherein the first monitored area and the second monitored area are adjacent. The base station is configured to determine a location of the pet as being in at least one of the first monitored area and the second monitored area based at least in part on the first and second data. The base station is configured to determine a status of the pet based on at least one of the first and second data.

Another embodiment relates to a system for monitoring a pet. The system includes a base station and a first monitoring device configured to capture first data relating to a first monitored area and to transmit the data to the base station. The system further includes a second monitoring device configured to be carried by the pet, the second monitoring device configured to capture second data relating to the pet and to transmit the data to the base station. The base station is configured to determine a location of the pet within the first monitored area based at least in part on the second data. The base station is configured to determine a status of the pet based on at least one of the first data and the second data.

An additional embodiment relates to a method of monitoring a pet with a pet monitoring system. The pet monitoring system includes a base station and a plurality of monitoring devices in communication with the base station. The method includes receiving, at the base station, a request to monitor the pet. The method includes activating, by the base station, the plurality of monitoring devices. The method further includes receiving, by the base station, data from the plurality of monitoring devices. The method includes determining, by the base station, a characteristic of the pet based on the data. The method includes performing, by the base station, an action in response to determining the characteristic of the pet.

Yet a further embodiment relates to a method of initiating a monitoring session between a user device and a pet monitoring system. The pet monitoring system includes a base station and a plurality of monitoring devices in communication with the base station. The method includes receiving, at the base station, a request to monitor the pet from the user device. The method further includes activating, by the base station, the plurality of monitoring device. The method includes receiving, by the base station, data from the plurality of monitoring devices. The method further includes locating, by the base station, the pet based on the received data from the plurality of monitoring devices. The method includes determining, by the base station, a characteristic of the pet. The method further includes selecting, by the base station, a selected monitoring device based upon at least one of the data from the plurality of monitoring devices and the location of the pet. The method includes transmitting, by the base station, the data from the selected monitoring device to the user device.

Another embodiment relates to a method of monitoring a pet with a pet monitoring system. The pet monitoring system includes a base station and a plurality of monitoring devices in communication with the base station. The method includes receiving, by the base station, data from the plurality of monitoring devices positioned at different positions within a monitored area, wherein the plurality of monitoring devices include a first camera and a second camera. The method further includes locating, by the base station, the pet based on the data received from the plurality of monitoring devices. The method includes determining, by the base station, that the pet is in a first field of view of the first camera. The method further includes monitoring, by the base station, the first field of view of the first camera. The method includes determining, by the base station, that the pet is no longer in the first field of view of the first camera and is in a second field of view of the second camera. The method further includes performing a handoff from the first camera to the second camera such that the base station monitors the second field of view of the second camera.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Referring to the figures generally, various embodiments disclosed herein relate to monitoring systems and methods. The monitoring systems and methods may be used to monitor a pet, such as a dog or a cat. The monitoring system may monitor the pet's movements, noises generated by the pet, the pet's health, the pet's actions, the pet's appetite, and the like. The monitoring system may utilize a system of sensors positioned at the location of the pet (e.g., the pet owner's home) such as microphones, cameras, radar, lidar, location sensors, and sensors coupled to the pet (e.g., on the pet's collar, implanted in the pet, etc.). The monitoring system may provide alerts, video, and other information and data to users (e.g., the pet's owner, a veterinarian, etc.) via remote user devices (e.g., a smartphone, a computer, a tablet, etc.). The monitoring system may also interact with the monitored animal by sending audible commands to the pet through a speaker system.

Figure 1:
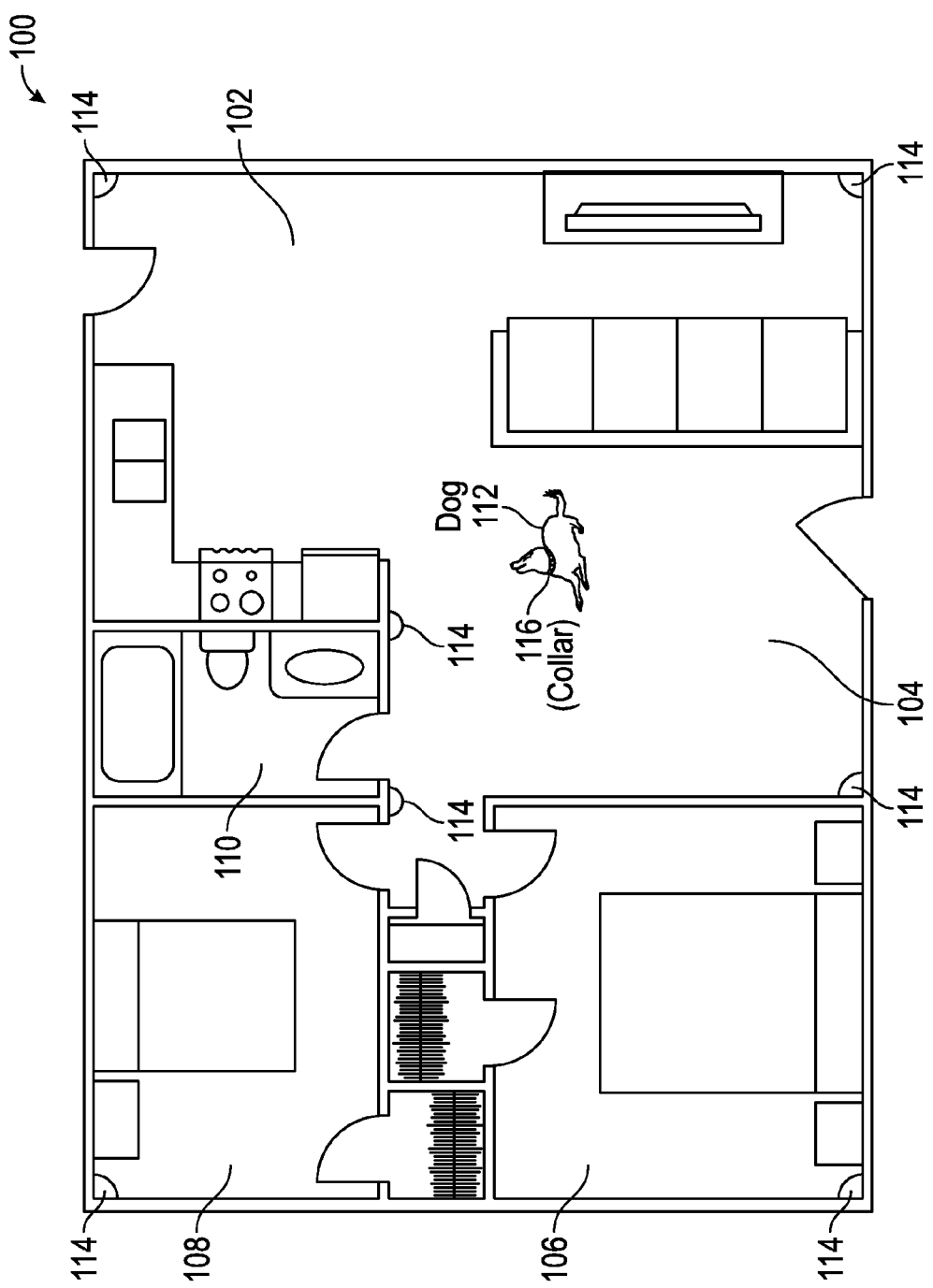
FIG. 1 is a schematic view of a living area floor plan.
Figure 2:
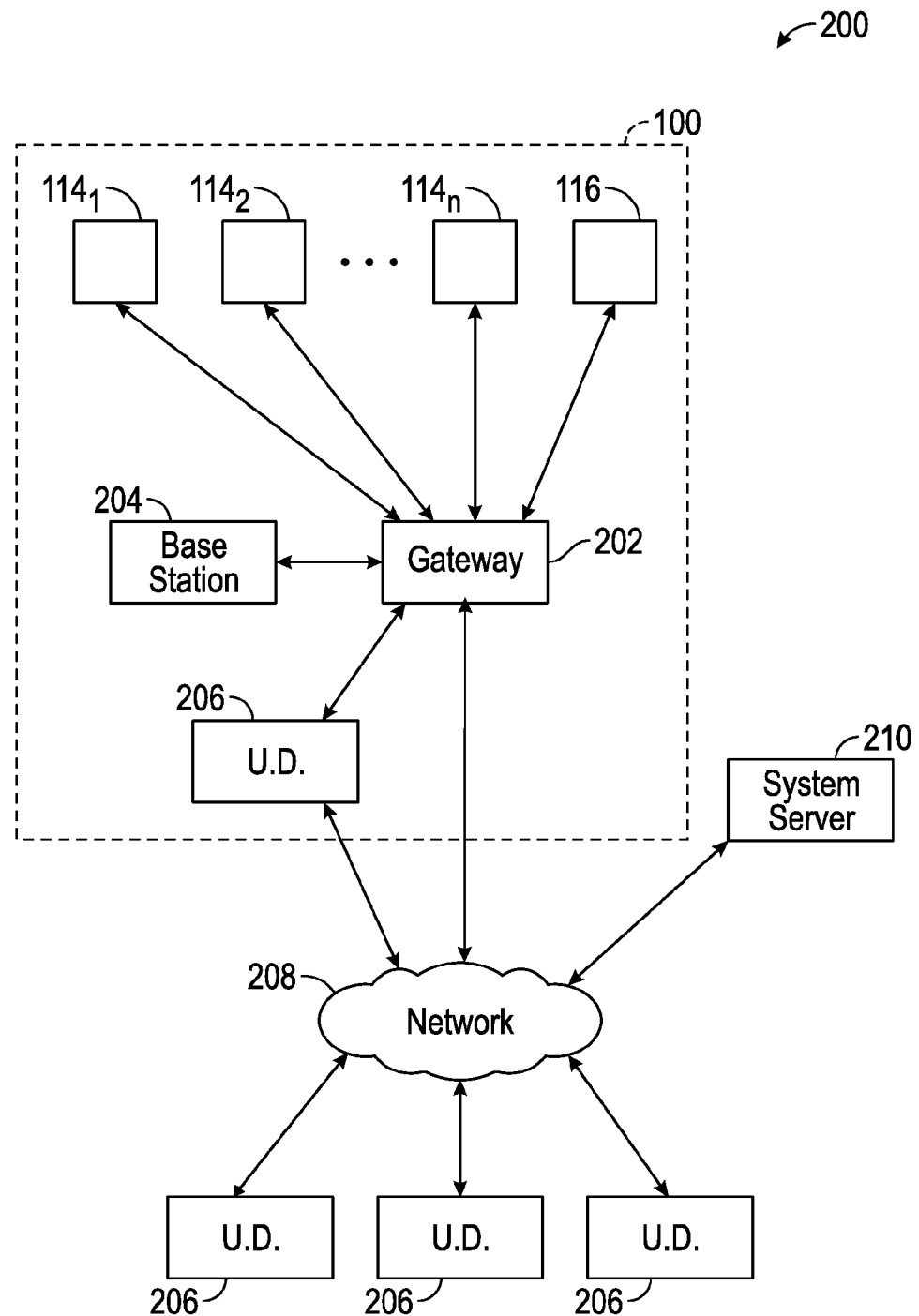
FIG. 2 is a schematic diagram of a monitoring system according to one embodiment.

Referring to FIG. 1, a floor plan of a living area 100 is shown. Living area 100 includes kitchen area 102, living area 104, a first bedroom 106, a second bedroom 108, and a bathroom 110. A pet 112 resides in living area 100. Living area 100 includes monitoring system 200 (as shown in FIG. 2). Monitoring system 200 includes a plurality of monitoring devices 114. In one embodiment, monitoring devices 114 include a single device (e.g., each monitoring device 114 may be one of a camera, a microphone, a radiofrequency receiver, a motion detector, a thermal imager, a radar device, a lidar device, an ultrasound device, a speaker, etc.). In another embodiment, one or more of the monitoring devices 114 includes a plurality of devices (e.g., any combination of cameras, microphones, radiofrequency receivers, motion detectors, thermal imagers, radar devices, lidar devices, ultrasound devices, speakers, odor emitters, pheromone emitters, etc.). Monitoring system 200 may also include monitoring device 116 coupled to pet 112 (e.g., on a collar of pet 112, implanted in pet 112, etc.). Monitoring devices 114 and 116 are configured to gather information and data regarding pet 112. The information and data regarding pet 112 may include location information, activity information, health information, image data, audio data, and the like. As described in further detail below, monitoring system 200 may provide the gathered information and data regarding pet 112 to a user (e.g., the owner of pet 112, a veterinarian, a neighbor, etc.). The information and data may be provided in an alert, in response to an on-demand request by the user, in a near real-time data stream, or another way as described herein.

Referring to FIG. 2, a block diagram of monitoring system 200 is shown. As discussed above, monitoring system 200 includes monitoring devices 114 and 116 that are located in living area 100. In one embodiment, monitoring system 200 also includes gateway 202 and base station 204. Gateway 202 may be a network access point within living area 100. For example, gateway 202 may be a user's existing wireless internet router. Gateway 202 may facilitate data communication between monitoring devices 114 and 116 and base station 204. Gateway 202 may form a local area network in facilitating the communication between monitoring devices 114 and 116 and base station 204. Gateway 202 may communicate with other devices using wired network standards (e.g., via Ethernet), wireless network standards (e.g., 802.11x, CDMA, GSM, LTE, Bluetooth®, ZigBee®, 802.15, etc.), or a combination thereof. Gateway 202 also facilitates data communication between base station 204 and a user device 206. Gateway 202 may communicate with a plurality of user devices 206. User devices 206 may be personal computers, laptops, PDAs, smartphones, tablet computers, portable media players, or the like. User device 206 may be located within living area 100 (and thus within direct communication range of gateway 202) or outside of living area 100. Accordingly, gateway 202 may communicate directly with user device 206 or indirectly through a wide area network 208. The wide area network 208 may be the Internet. Gateway 202 may also facilitate communication between base station 204 and the plurality of user devices 206 with a system server 210.

Monitoring system 200 may be programmed with location information relating to the positioning of monitoring device 114 within living area 100. A user may program the monitoring system 200 with position information relating to monitoring device 114 through user device 206 or through base station 204. In some arrangements, the user may program the position information through interaction with an interactive floor plan of living area 100. The position information may be stored in a memory of base station 204, a memory of monitoring device 114, a memory of system server 210, or a combination thereof. In some situations, monitoring system 200 may automatically determine position information based on analyzing images and/or position data received from monitoring device 114. The position information may include a room identifier (e.g., "living room," "family room," etc.), a height off of the floor of living area 100, spatial information relating to the distance between monitoring device 114 and another monitoring device 114, orientation information, and the like. The location information may be used by the monitoring system 200 to perform monitoring device handoffs. For example, as pet moves 112 between rooms or areas of living area 100, monitoring system 200 may automatically activate (e.g., instruct the capture of information) monitoring devices 114 positioned within a monitoring range of pet 112 and deactivate monitoring devices that are out of monitoring range of pet 112.

Generally, during monitoring operations, base station 204 selectively instructs the monitoring devices 114 to record information relating to pet 112. The base station 204 receives information relating to the pet 112 from the plurality of monitoring devices 114 and from monitoring device 116. The information relating to pet 112 may be routed through gateway 202. In some arrangements, base station 204 may communicate directly with monitoring devices 114 and 116 (e.g., in a short-range wireless communication system). Base station 204 analyzes and stores received information relating to pet 112. In some arrangements, base station 204 transmits the received information relating to pet 112 to system server 210 for storage and analysis. Based on the analysis of the information relating to pet 112, base station 204 may initiate an alert to a user via at least one of the plurality of user devices 206, may activate, deactivate, or adjust each of the plurality of monitoring devices 114 on an individual basis, may initiate an alert to pet 112 through at least one of the plurality of monitoring devices 114 and 116, may stream data to a user device, may alert a third-party, or perform another function. The specifics of the operation of monitoring system 200 are described in further detail below with respect to FIGS. 3 through 8.

Figure 3:
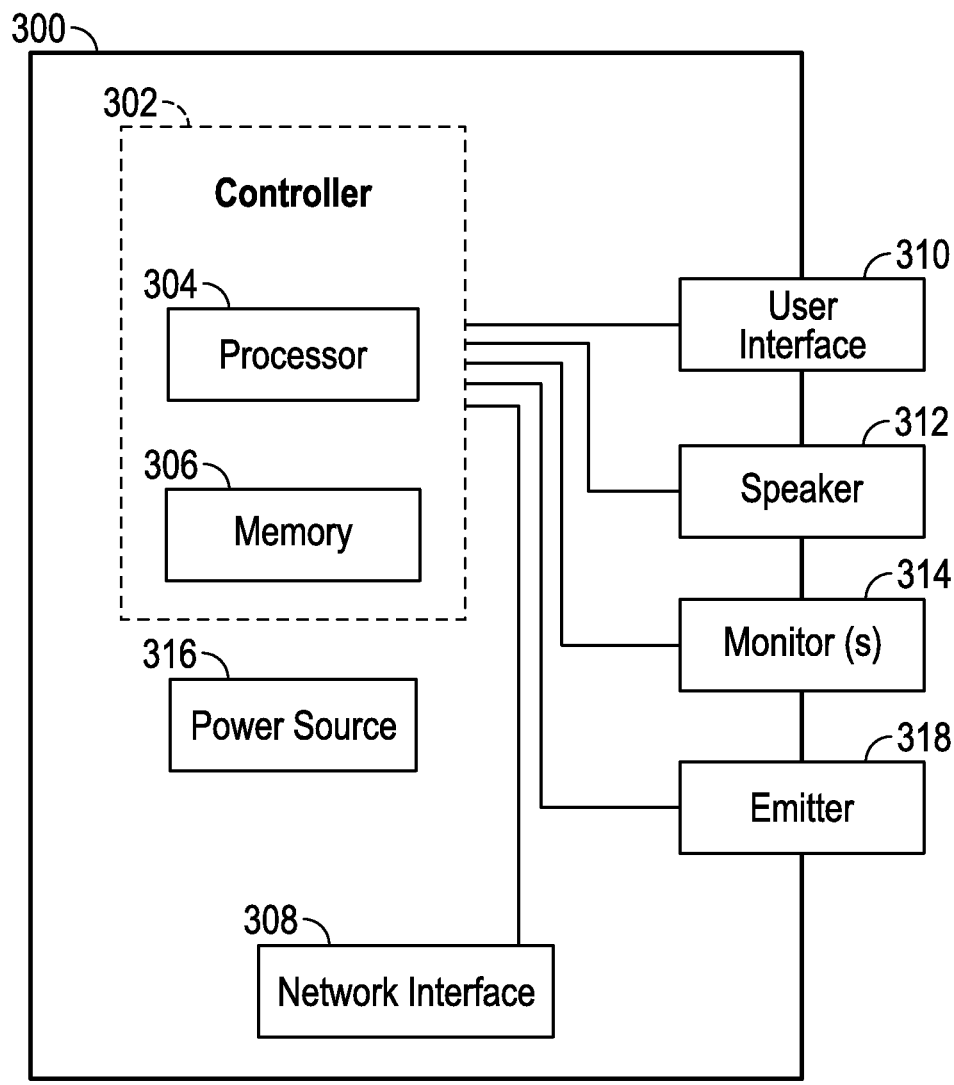
FIG. 3 is a block diagram of a monitoring device of the monitoring system of FIG. 2.

Referring to FIG. 3, a block diagram of monitoring device 114 is shown. Monitoring device 114 includes a housing 300. Housing 300 may be sized and shaped for placement in various positions within living area 100. For example, in certain arrangements, housing 300 is shaped like a domed security camera for mounting on a wall or a ceiling of living area 100. In other arrangements, housing 300 is integrated into other devices already found in living area 100, such as smoke detectors, alarm clocks, light fixtures, or the like. Housing 300 contains the working components of monitoring device 114.

The operation of monitoring device 114 is controlled by controller 302. Controller 302 includes processor 304 and memory 306. Memory 306 stores operating instructions that, when executed by processor 304, control the operation of monitoring device 114. Controller 302 is in communication with network interface 308. In some arrangements, network interface 308 may be integrated with controller 302 (e.g., controller 302 may be a system-on-chip controller). Network interface 308 may include a wired network interface (e.g., an Ethernet port), a wireless network interface (e.g., 802.11a/b/g/n, CDMA, GSM, LTE, Bluetooth®, ZigBee®, 802.15, etc.), or a combination thereof. Network interface 308 is configured to enable two-way data transmission between monitoring device 114 and base station 204 and/or gateway 202. Controller 302 is also in communication with user interface 310, speaker 312, and monitor(s) 314. User interface 310 is configured to allow a user to program certain aspects monitoring device 114. For example, user interface 310 may allow a user to establish a connection between monitoring device 114 and gateway 202. Accordingly, user interface may include a button (e.g., a Wi-Fi Protected Setup button). User interface 310 may include a status indicator, such as an LED and/or a display panel. Speaker 312 is configured to emit sound. The sound may be audible to humans or inaudible to humans (e.g., the sound may be emitted at ultrasonic frequencies). Speaker 312 may be used in sending audible alerts to a user and/or pet 112.

Monitor(s) 314 are configured to monitor pet 112. As discussed above, in some arrangements, monitoring device 114 includes a single monitor 314 (e.g., monitoring device 114 may only function as a camera). In other arrangements, monitoring device 114 includes a plurality of monitors 314. Monitor(s) 314 may include any combination of cameras (video and still cameras), microphones, radiofrequency receivers, RFID readers, motion detectors (e.g., passive infrared, active infrared, ultrasonic, radar, etc.), thermal imagers, radar position tracking devices, lidar position tracking devices, ultrasound position tracking devices, beacon position tracking devices, and the like. Each of the monitor(s) 314 captures information relating to pet 112 and the environment of living area 100. The captured information is provided to controller 302 for transmission to base station 204 through network interface 308 where the captured information may be analyzed and processed to determine pet locations and activities.

In some arrangements, monitoring device 114 includes emitter 318. Emitter 318 may be an odor emitter or a pheromone emitter or generating device. In such arrangements, monitoring device 114 is programmed to emit various odors or pheromones based on detected activities and/or user commands. The odors or pheromones may be any of the scent of food, the scent of another animal, the scent of the pet's owner, alarm pheromones, trail pheromones, sex pheromones, aggregation pheromones, epideictic pheromones, releaser pheromones, signal pheromones, primer pheromones, territorial pheromones, and the like. The emitted odors or pheromones may cause pet 112 to be attracted to an area of monitoring device 114, repelled from the area of monitoring device 114, and/or change a behavior of pet 112. Emitter 318 may be a light source, or a visual image source such as a display or a projector. In such arrangements, monitoring device 114 is programmed to emit various lights or images based on detected activities and/or user commands. The lights may include colors selected to change a behavior of the pet, and may provide steady illumination or may be pulsed in a pattern selected to change a behavior of the pet. The visual image source may emit visual images selected to change a behavior of the pet, such as images of the pet's owner, images of another animal, images of food, or the like.

Monitoring device 114 is powered by power source 316. Power source 316 may be contained within housing 300 or may be external to housing 300. Power source 316 may include a battery. The battery may be rechargeable. Power source 316 may be connected to the power grid of living area 100. Power source 316 may include any necessary voltage and current converters to supply power to controller 302, network interface 308, user interface 310, speaker 312, and monitor(s) 314.

Figure 4:
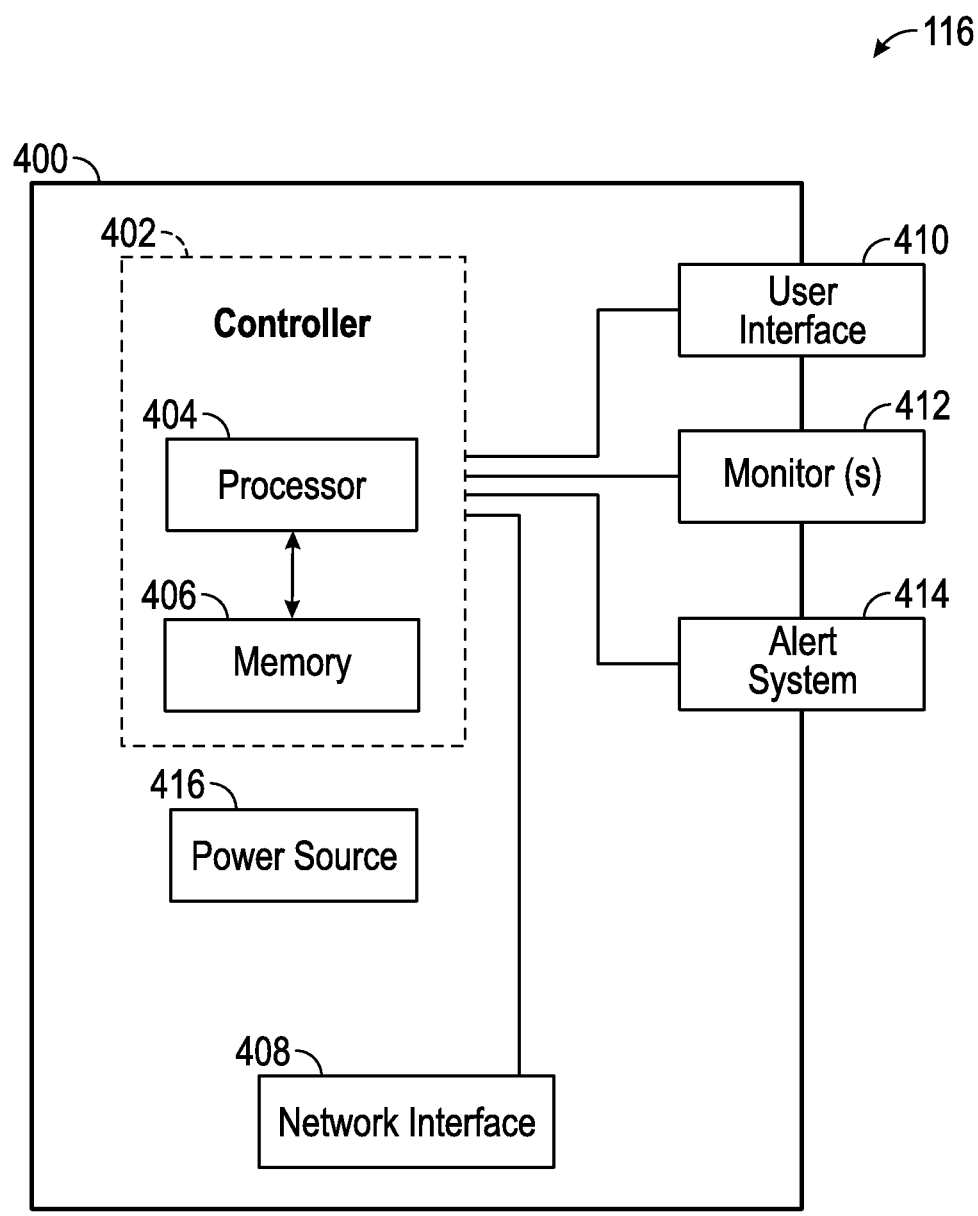
FIG. 4 is a block diagram of a monitoring device of the monitoring system of FIG. 2.

Referring to FIG. 4, a block diagram of monitoring device 116 is shown. Monitoring device 116 is similar to monitoring device 114. However, monitoring device 116 is configured to be worn by, implanted in, or otherwise affixed to pet 112. As described below, monitoring device 116 may also include different sensors as monitoring device is coupled to pet 112. Monitoring device 116 may also include one or more pet location devices. In some arrangements, the pet location devices includes a beacon (e.g., emitting ultrasound, radiofrequency waves, or light waves such as infrared, visible, or ultraviolet light) whose output is detectable by one or more monitoring devices 114. The beacon may continuously emit such waves, or may emit under command of the base station (e.g., only when the base station desires to determine the pet's location). In some embodiments, the pet location devices include a GPS receiver, an RFID tag, or an inertial sensor such as an accelerometer or a gyroscope. Monitoring device 116 includes housing 400. Housing 400 may be sized and shaped for placement in a pet collar, in a pet harness, or for implanting in a pet. The operation of monitoring device 116 is controlled by controller 402 in the same manner as described above with respect to controller 302. Accordingly, controller 402 includes processor 404 and memory 406. Memory 406 stores operating instructions that, when executed by processor 404, control the operation of monitoring device 116. Controller 402 is in communication with network interface 408. Network interface 408 may be integrated with controller 402. Network interface 408 may include a wireless network interface (e.g., 802.11a/b/g/n, CDMA, GSM, LTE, Bluetooth®, ZigBee®, 802.15, etc.). Network interface 408 is configured to enable two-way data transmission between monitoring device 116 and base station 204 and/or gateway 202. Controller 402 is also in communication with user interface 410, monitor(s) 412, and pet alert system 414. User interface 410 is configured to allow a user to program certain aspects monitoring device 116. User interface may include a button (e.g., a Wi-Fi Protected Setup button). User interface 410 may include a status indicator, such as an LED and/or a display panel. Monitoring device 116 is powered by power source 416. Power source may include a battery. The battery may be rechargeable.

Monitor(s) 412 are configured to monitor pet 112. In some arrangements, monitoring device 116 includes a single monitor 412 (e.g., location tracking device). In other arrangements monitoring device 116 includes a plurality of monitors 412. Monitor(s) 412 may be movement detectors, pet biometric or vital monitors (e.g., heartbeat monitor, blood pressure monitor, thermometer, etc.), position tracking devices (e.g., GPS tracking systems, beacon tracking systems, and the like). Each of the monitor(s) 412 captures information relating to pet 112. The captured information is provided to controller 402 for transmission to base station 204 through network interface 408 where the captured information may be analyzed and processed to determine pet locations and activities.

Alert system 414 may be used to send an alert to pet 112. As discussed in further detail below, monitoring system 200 may be configured to send alerts to pet 112. The alerts may be triggered automatically (e.g., based on a detected activity of pet 112), or as a result of an on-demand request from a user of monitoring system 200. In one embodiment, the alert is an audible alert, in which case the alert system 414 includes a speaker. In an alternative embodiment, the alert is a vibratory alert, in which case the alert system 414 includes a vibration mechanism. In other arrangements, the alert is an electric shock, in which case the alert system 414 includes a shocking device. The details of pet shocking devices are known to those skilled in the art. The shocking device is configured to provide a non-lethal electric current. In other arrangements, the alert is an olfactory alert, in which case the alert system 414 is configured to release a scent or pheromone. In other arrangements, the alert is a visual alert, in which case the alert system 414 is configured to emit a light or a visual image. The alert sent through alert system 414 is initiated by at least one of base station 204 and controller 402.

Figure 5:
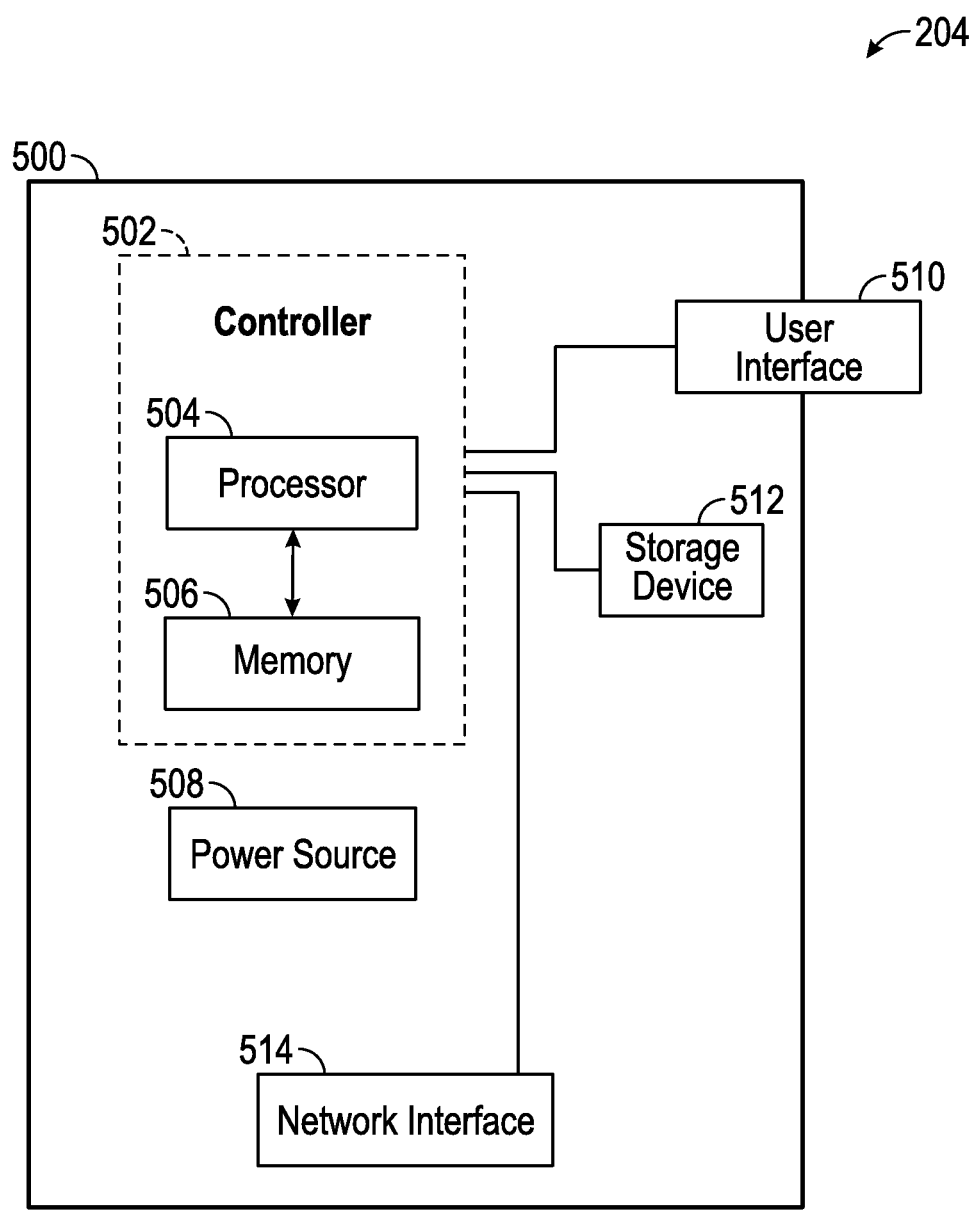
FIG. 5 is a block diagram of a base station of the monitoring system of FIG. 2.

Referring to FIG. 5, a block diagram of base station 204 is shown. Base station 204 may be a stand-alone computing device configured to interact with monitoring devices 114 and 116 and gateway 202. In some arrangements, base station 204 may be a personal computer of the owner of living area 100. In such an arrangement, a monitoring system program may be running on the personal computer. In other arrangements, base station 204 only serves as a base station for monitoring system 200. Base station 204 includes housing 500. The operation of base station 204 is controlled by controller 502 in the same manner as described above with respect to controllers 302 and 402. Accordingly, controller 502 includes processor 504 and memory 506. Memory 506 stores operating instructions that, when executed by processor 504, control the operation of monitoring device 204. Controller 502 is in communication with network interface 508. Network interface 508 may be integrated with controller 502. Network interface 508 may include a wired network interface (e.g., an Ethernet port), a wireless network interface (e.g., 802.11a/b/g/n, CDMA, GSM, LTE, Bluetooth®, ZigBee®, 802.15, etc.), or a combination thereof. Network interface 508 is configured to enable two-way data exchange with monitoring devices 114 and 116 and and/or gateway 202. Controller 502 is also in communication with user interface 510 and storage device 512. User interface 510 is configured to allow a user to program certain aspects monitoring system 200. In some arrangements, user interface 510 is configured to allow a user to view stored information regarding pet 112. Information received from monitoring devices 114 and 116 may be stored in storage device 512 and accessed by a user via user interface 510. User interface 510 may include a display and an input (e.g., a keyboard and a mouse). In some arrangements, the user interface 510 may include a touchscreen display. Base station 204 is powered by power source 514. Power source 514 may include a battery. The battery may be rechargeable. Power source 514 may be connected to the power grid of living area 100.

During operation, base station 204 communicates with monitoring devices 114 and 116, system server 210, and user devices 206. Base station 204 receives information and data relating to pet 112 from monitoring devices 114 and 116. The information and data is processed and analyzed by base station 204 to determine locations, characteristics, and activities of pet 112. In an alternative embodiment, base station 204 serves as a data and information relay and transmits the data and information to the system server 210 for analysis and processing. In certain embodiments, base station 204 may initiate alerts to and two-way communication sessions with users via user devices 206. The details of operations are described in further detail below.

Figure 6:
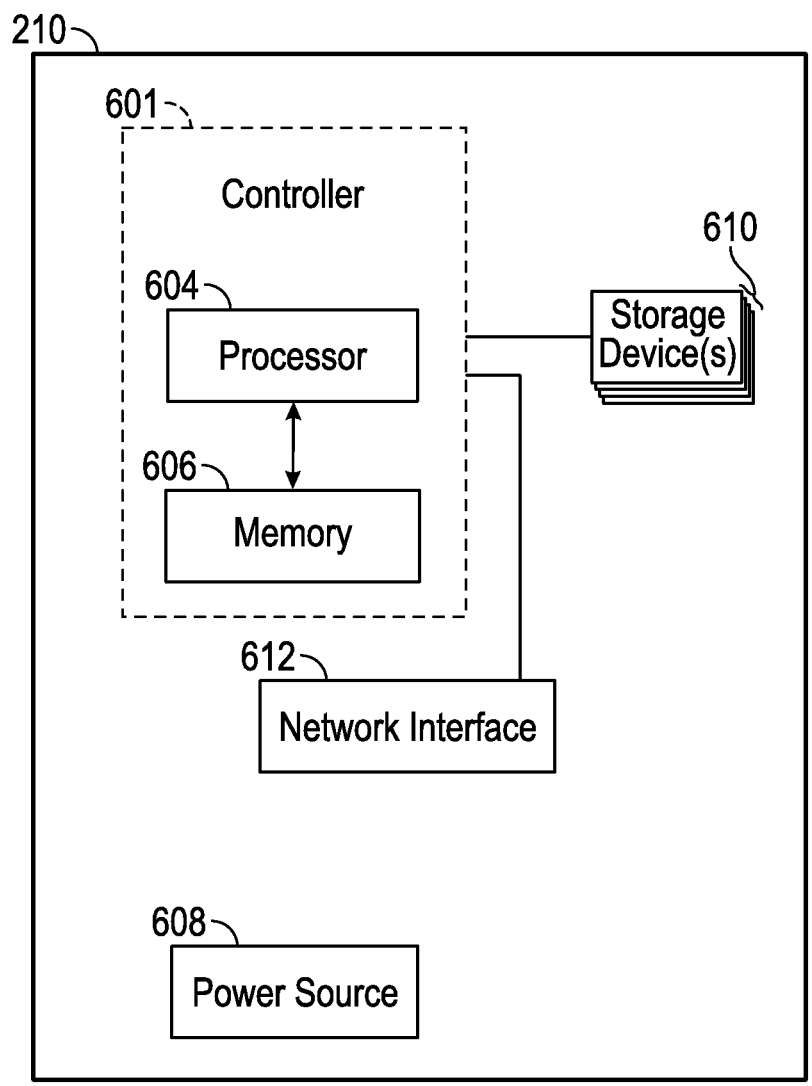
FIG. 6 is a block diagram of a system server of the monitoring system of FIG. 2.

Referring to FIG. 6, a block diagram of system server 210 is shown according to one embodiment. System server 210 includes controller 602. Controller 602 controls the operation of system server 210. Control 602 includes processor 604 and memory 606. Memory 606 stores operating instructions that, when executed by processor 604, control the operation of system server 210. System server 210 includes network interface 608. Network interface 608 is configured to communicate with base station 204 via network 208 and gateway 202. Network interface 608 may communicate using wired network standards (e.g., via Ethernet), wireless network standards (e.g., 802.11x, CDMA, GSM, LTE, Bluetooth®, ZigBee®, 802.15, etc.), or a combination thereof. System server 210 includes storage devices 610. System server 210 includes power source 612. Power source 612 provides operational power to system server 210. Power source 210 may receive power from an external power grid.

Storage devices 610 store data relating to monitoring system 200. Storage devices 610 may include a plurality of hard drives. Storage devices 610 may store user account information and information relating to pet 112. The information relating to pet 112 may be associated with a user account (e.g., the user account of the owner of pet 112) in a database stored within system server 210. The information may be retrieved by users via user devices 206.

Figure 7:
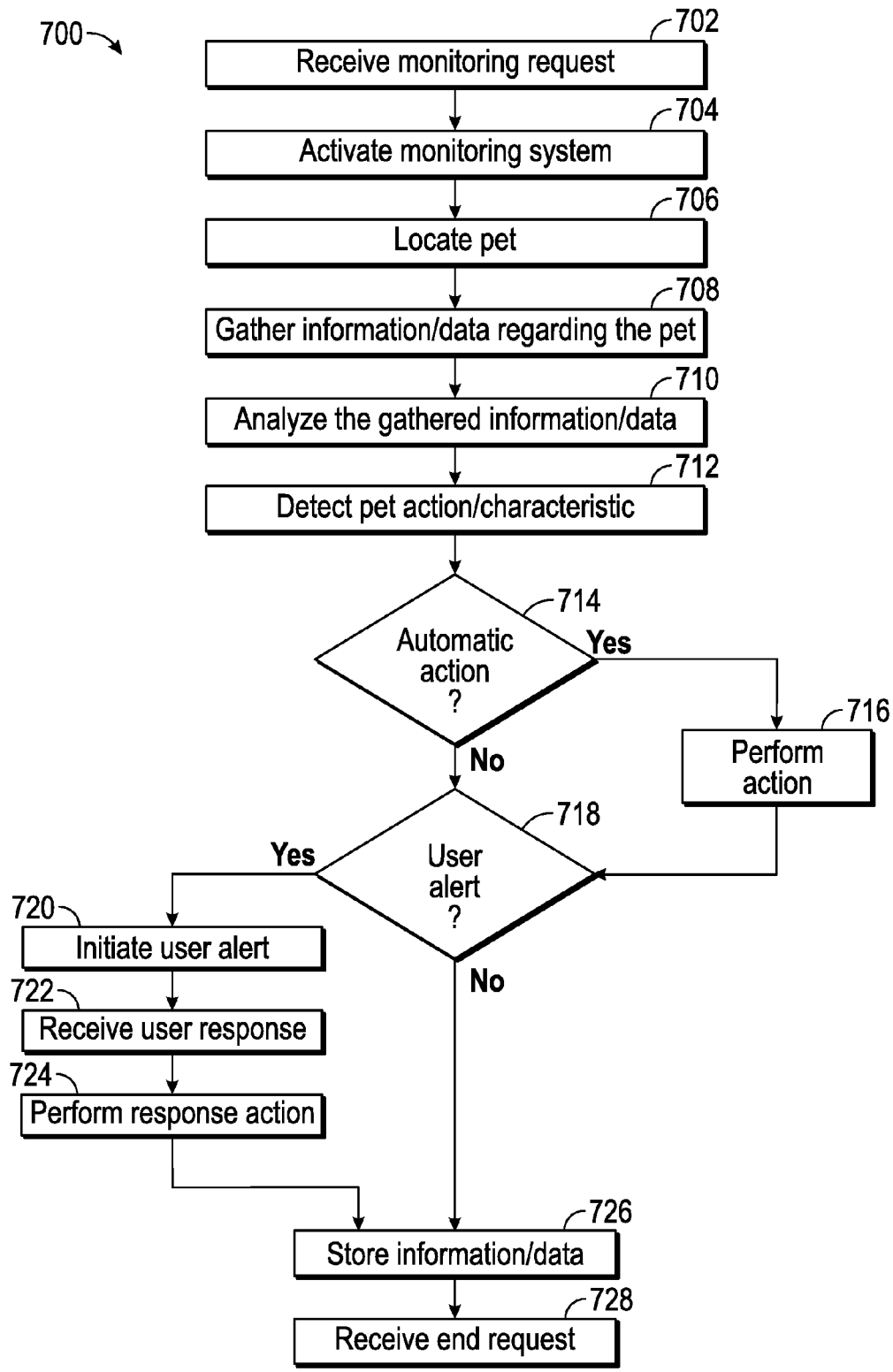
FIG. 7 is a flow diagram of a method of monitoring a pet with a monitoring system.

Referring to FIG. 7, method 700 of autonomously monitoring a pet with a pet monitoring system (e.g., monitoring system 200) is shown according to one embodiment. As described below, method 700 may be performed by a base station (e.g., controller 502 of base station 204) that is in communication with a plurality of monitoring devices (e.g., monitoring devices 114 and 116). In an alternative arrangement, method 700 may be performed by a system server (e.g., controller 602 of system server 210) that is in communication with the base station via a network (e.g., network 208).

A monitoring request is received (702). The monitoring request may be received via a user input at a base station. In an alternative arrangement, the monitoring request is received from a user device (e.g., user device 206) that is in communication with the base station. The request includes a request to monitor a pet via the monitoring system. For example, a user may send a command from his cell phone via a text message or an application running on the cell phone to begin monitoring of a pet. The request may include a schedule for monitoring the pet (e.g., a request to monitor the pet over a certain time period selected by the user). In some arrangements, the request may be initiated by an external computing program that has been programmed with a monitoring schedule by the user (e.g., a scheduler or calendar program associated with the user). The request may include monitoring preferences, including allowed and not allowed activities for the pet (e.g., the pet is not to enter a specified room, the pet is not to sit on the couch, etc.). The request may include alert preferences (e.g., that the user would like to receive an alert if one of the not allowed activities is detected, when a third-party should be alerted, when a pet should be alerted, etc.). The monitoring preferences and the alert preferences may be stored in a user account that is accessible by the base station. The user account may be stored in a database on the base station or in a database on the system server. Accordingly, the base station may instruct monitoring via the monitoring system according to the monitoring preferences and alert preferences associated with the user account.

After the request is received, the monitoring system is activated (704). The monitoring system may be activated by a base station. The monitoring system may include a plurality of monitoring devices, such as monitoring devices 114 and 116 as discussed above with respect to FIG. 1. The monitoring devices may include cameras, microphones, radiofrequency receivers, speakers, location sensors, or combinations thereof (as described above with respect to monitoring devices 114 and 116). The monitoring devices are configured to gather information about a pet within a monitored area (e.g., living area 100). The information regarding the pet may include location information, activity information, health information, and the like. The monitoring devices may be in wireless or wired communication with the base station. Accordingly, the base station may send a command directly to each monitoring device to activate each monitoring device.

Once the monitoring system is activated, the monitoring system is instructed to locate a pet associated with the monitoring request (706). In some embodiments, the instruction is sent from a base station to at least one monitoring device of the monitoring system. The pet may be located via a monitoring device configured to locate the pet. For example, the pet may be wearing a collar that transmits location information to the base station (e.g., monitoring device 116). In other arrangements, a system of cameras and microphones may locate the pet based on analyzing at least one of captured images and audio regarding the pet. In certain situations, a household may have multiple pets and the monitoring request may correspond to a single target pet. In such situations, the base station may be able to identify the target pet based on user programmed biometric information about the pet (e.g., pet size, fur color, audio signatures, etc.) stored within the monitoring system. The information received from the monitoring devices may be compared against the programmed biometric information to identify the target pet. The monitoring system may be able to differentiate pets from other living objects, such as humans, based on detected information (e.g., image analysis, thermal image analysis, etc.). After locating the pet, the system may hone in on the pet with the monitoring devices. For example, the monitoring devices may include cameras having pan, tilt, illumination, and zoom functions, which may be adjusted to image the pet (e.g., the pan, tilt, illumination, and zoom functions of a monitoring device may be individually adjusted to maintain a specified image quality of the pet within the monitoring area of the monitoring device as the system determines the location of the pet is shifting).

Additionally, as the pet moves from a first room, area, or field of view to a second room, area, or field of view (e.g., from the first bedroom 106 to the second bedroom 108), handoffs may be performed from a first monitoring device to a second monitoring device to allow for continuous monitoring of the pet even as the pet moves out of the field of view of a first monitoring device. Handoffs may allow the monitoring system to analyze only the data and information relating to the pet and to disregard (i.e., not analyze) the data and information not relating to the pet (e.g., information and data captured relating to an empty room that the pet is not in). Such data and information analysis may save network bandwidth during transmission of the analyzed data and information (e.g., to a remote user device, to a system server, etc.) and may additionally save storage space when storing the analyzed data and information. For example, the monitoring system may automatically store, monitor, or transmit only the data from a first monitoring device when the pet is in the field of view of the first monitoring device. If the pet moves out of the field of view of the first monitoring device, the monitoring system may perform a handoff to a second monitoring device having a second field of view that includes the pet. Accordingly, handoffs may be performed as the pet moves such that only data including the pet is stored, monitored, or transmitted, and such that data from monitoring devices not capturing data or information regarding the pet may be discarded by the monitoring system.

After locating the pet, information and data regarding the pet is gathered (708). The information and data is gathered by the monitoring devices and is transmitted to the base station. In some arrangements, the gathered information and data is transmitted from the base station to a monitoring system server (e.g., system server 210). The information and data regarding the pet may include location information. The location information may relate to a detected room where the pet is present (e.g., that the pet is in the living area 104), GPS coordinates, or the like. The information and data regarding the pet may include activity information. For example, an on-pet monitor (e.g., monitoring device 116) may include a motion sensor capable of detecting the pet's acceleration, the pet's speed of movement, the pet's orientation, and the like. Alternatively or additionally, the monitoring system may be able to determine the activity information by monitoring image data captured through cameras used to track the pet (e.g., monitoring devices 114). The information and data regarding the pet may include health information. For example, an on-pet monitor (e.g., monitoring device 116) may be able to monitor a pet's heart rate, temperature, blood pressure, respiratory rate, and the like. The information and data regarding the pet may include image data. As noted above, the monitoring devices may include cameras. The cameras may capture image data concerning the pet. The image data may include still image data, video image data, thermal image data, or a combination thereof. The information and data regarding the pet may include audio data.

The gathered information and data is analyzed (710). The information and data may be analyzed by the base station or by the central server. The base station or the central server may analyze the gathered information and data in approximately real-time. The gathered information and data is analyzed to detect pet actions, inactions, or characteristics based on predefined profiles for actions and characteristics. For example, the gathered information and data may be analyzed to determine that a pet has entered an area where the pet is not allowed (i.e., the user programmed the monitoring system to indicate that the pet is not allowed access to the area). As additional examples, the gathered information and data may be analyzed to determine a physical status of the pet, such as a health characteristic of the pet, what the pet is currently doing (e.g., eating, sleeping, running around, playing with another pet, sitting on a couch, barking, howling, having an accident, urinating, defecating, fighting with another pet, eating food belonging to a human or to another pet, damaging furniture or other objects, etc.), or another status of the pet. The status or activity of the pet may be compared to actions specified by a system user, such as poses, postures, tricks or the like which the user wants imaged or to be informed about.

During analysis of the gathered information and data, a pet action or characteristic is detected (712). The pet action or characteristic may relate to the pet entering an area in which the pet is not allowed, the pet exceeding a normal threshold of activity (e g, running in the house), the pet eating or drinking (e.g., its food, or restricted food such as that belonging to a human or to another pet), the pet damaging an item in the house, the pet making a lot of noise (e.g., barking, howling, meowing, etc.), the pet urinating or defecating in the house, the pet having poor health vitals, or the like. The monitoring system determines whether an automatic action is to be taken depending on the detected action (714).

Under certain circumstances, an automatic response is performed (716). The automatic action may include generating noise or an audible alert to the pet. For example, if the detected action or characteristic relates to the pet entering an area in which the pet is not allowed, the monitoring system may generate a noise to attract the pet to a different area or to scare or shoo the pet out of the not-allowed area. The noise may relate to a tone. The noise may be audible to humans or inaudible to humans (e.g., ultrasonic). For example, the tone may be an ultrasonic tone, which is commonly referred to as a dog whistle. The noise may relate to a prerecorded voice message. For example, a user of the system may pre-record an audio message, such as "Bad dog!" or "Come here!," which may then be played over a speaker of the monitoring in response to the detected action or characteristic. The noise may be a directional noise. In some embodiments, directional noise may be provided by emitting directed ultrasonic noises which are selected so as to undergo frequency conversion (e.g., in the air or in the pet's tissue) to specified audible noises. In other embodiments, directional noise may be provided by emitting sounds from designated speakers, or by coordinated activation of multiple speakers. For example, a monitored area may have a plurality of speakers (e.g., a plurality of monitoring devices 114 spaced out amongst a plurality of different areas of a monitored area). If the purpose of the noise is to attract the pet to a designated area, a noise may be generated in the designated area, which may be at an opposite end of the monitored area from where the pet is located. If the purpose of the noise is to encourage a pet to leave an area, the noise may be generated in the area where the pet is located.

The automatic action may include emitting an odor or a pheromone from the monitoring device. The odor or pheromone is emitted from an emitter (e.g., emitter 318) of the monitoring device. The odors or pheromones may be any of the scent of food, the scent of another animal, the scent of the pet's owner, alarm pheromones, trail pheromones, sex pheromones, aggregation pheromones, epideictic pheromones, releaser pheromones, signal pheromones, primer pheromones, territorial pheromones, and the like. The emitted odors or pheromones may cause the pet to be attracted to an area of the monitoring device, repelled from the area of the monitoring device, and/or change a behavior of the pet. In other embodiments, the automatic action may include emitting a light or a visual image from the monitoring device, or may include shocking the pet via a shocking device worn by the pet.

The automatic action may include alerting a third-party. The alert sent to the third-party may be a message. For example, if the detected action or characteristic relates to the pet having poor health vitals, the monitoring system may initiate a message to a veterinarian or an emergency contact (e.g., a neighbor). The message may be an e-mail message or a text message. The message may include any combination of a description of the pet (e.g., type of pet, name of the pet, age of the pet, size of the pet, etc.), an indication of the detected characteristic or action, a time of the detected characteristic or action, and the current location of the pet. The message may include a recent photo or a video of the pet as captured from a monitoring device. The message may be an automated phone call having an audio message. The contents of the audio message may include any of the above identified contents of the written message (e.g., as generated from a text-to-speech module of the monitoring system). The third-party may be designated by the user of the monitoring system. The user may designate third-parties to contact for different detected events. For example, the user may program the monitoring system with contact information for a veterinarian and a neighbor. The veterinarian may be contacted for a first set of detected activities or characteristics (e.g., the veterinarian may be contacted only for health related issues), while the neighbor may be contacted for a second set of detected activities or characteristics. The monitoring system may store the user's programmed third-party contact preferences.

The system determines whether an alert to a user is to be initiated (718) Depending on the detected action, the monitoring system may initiate a user alert for action needed depending on the detected action. In the determined pet characteristic matches an alert scenario (e.g., a preprogrammed alert scenario, a specified pet characteristic, etc.), an alert is initiated to a user (720). The user alert may be initiated in addition to automatically performing an action (as done in 716). The alert may include at least one of a message, such as an e-mail or a text message or, and an automated phone call having an audio message. The contents of the initiated alert may be the same as described above with respect to the third-party alert (as described above with respect to 716). The user alert may include a request for the user to reply. For example, the monitoring system may inquire as to whether the user would like the system to perform another action, such as sending an audible alert to the pet or alerting a third party. The user may reply by sending a reply message back to the monitoring system. The reply message may be sent via e-mail or text message in reply to a received e-mail or text message. The reply message may be initiated through a smartphone application. The reply message may be initiated by the user by responding to a prompt during a telephone message (e.g., by pressing a button on the phone or by speaking into the phone). In some situations, the user may have the ability to record a message that the monitoring system may transmit to a third-party or may play to the pet over a speaker of the monitoring system. The user may also have the ability to enter into a two-way communication session with the monitoring system (e.g., as described below with respect to method 800).

Accordingly, the monitoring system may optionally receive a response from the user (722). As discussed above, the response may include an instruction for the monitoring system to perform an action. If the response includes an instruction to perform an action, such as sending an audible alert to the pet, alerting a third-party, or enter a two-way communication session, the monitoring system performs the user requested action (724). The user requested action may be performed in the same manner as discussed above with performing the automatic action (716).

Throughout the monitoring process, the gathered information and data is stored (726). The gathered information and data may be stored locally at the base station or may be stored remotely at the system server. The information and data may be permanently stored or temporarily stored. The monitoring system may automatically determine whether to permanently or temporarily store the information and data based on the pet activities or characteristics to which the data and information correlate. For example, if the information and data correlates to the pet sleeping, the information and data likely is not important information and data. Accordingly, the monitoring system may automatically discard this data and information after a designated period of time (e.g., after an hour). If the information and data correlates to an important pet activity, such as a pet health issue, the information and data may be permanently stored until the user instructs the monitoring system to delete the information and data. Stored information and data may be compressed or may undergo further processing (e.g., decreasing recording quality) to reduce the amount of storage space required to store the information and data. The stored information and data may be selectively compressed or may selectively undergo a reduction in quality based on the whether the data and information correlates to a non-event pet activity or characteristic (i.e., data and information relating to non-events of the pet, such as the pet sleeping or behaving normally, may be reduced in quality and/or compressed to reduce the storage space requirement of the non-event data and information). The stored information and data may be ranked, based on the determined characteristic. The ranking can be based on correlating the determined characteristic to a specified characteristic. For example, the user or system may consider some forms of pet characteristics or activities more significant than others (e.g., urination on furniture can rank higher than sleeping) and specify a ranking order for such characteristics or activities. This ranking can be used to prioritize the stored data with regard to displaying the data to the user, transmitting it to the user, or storing it.

Each of the above identified steps may be repeated throughout the duration of the monitoring process. The monitoring process continues until a stop command is received by the monitoring system (728). The stop command may be sent to the base station based on the passage of a scheduled stop time (e.g., a previously specified date and time, the expiration of a timer, etc.) or based on a user command. The user command may be initiated via a remote device. For example, the user may initiate the stop command from an application running on a smartphone. In an alternative arrangement, the user may interface directly with the base station to input a stop command.

Figure 8:
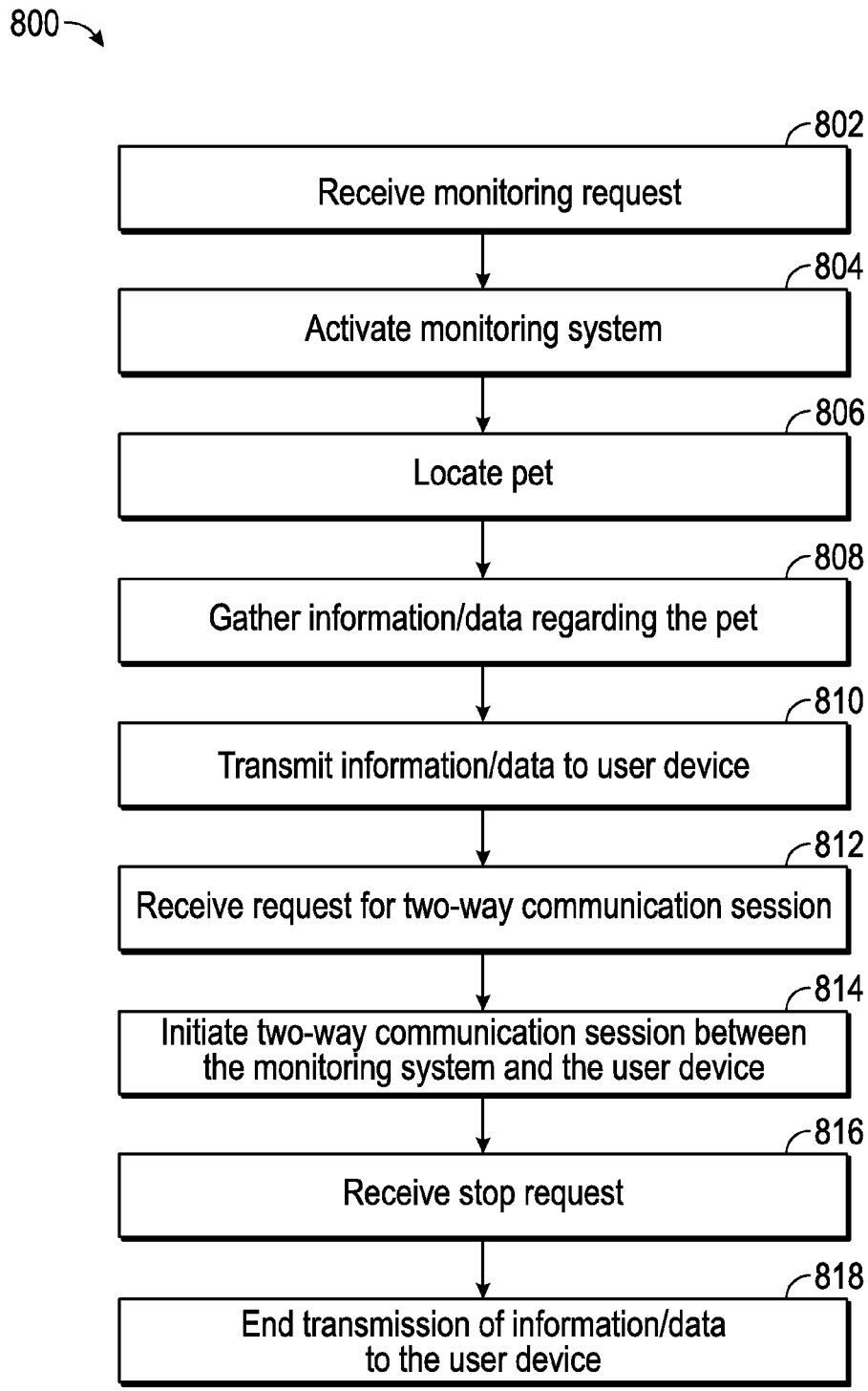
FIG. 8 is a flow diagram of a method of streaming data regarding a monitored pet and imitating a two-way communication session with a monitoring system.

Referring to FIG. 8, method 800 of streaming data regarding a monitored pet with a pet monitoring system (e.g., monitoring system 200) and initiating a two-way communication session is shown. As described below, method 800 may be performed by a base station (e.g., controller 502 of base station 204) that is in communication with a plurality of monitoring devices (e.g., monitoring devices 114 and 116). In an alternative arrangement, method 800 may be performed by a system server (e.g., controller 602 of system server 210) that is in communication with the base station via a network (e.g., network 208). In some arrangements, method 800 may be performed as part of method 700.

A monitoring request is received (802). The monitoring request may be received from a base station. The monitoring request may be received via a user input at a base station. In an alternative arrangement, the monitoring request is received from a user device (e.g., user device 206) that is in communication with the base station. The request includes a request to monitor a pet via the monitoring system. For example, a user may send a command from his cell phone via a text message or an application running on the cell phone to begin monitoring of a pet. The request may include a schedule for monitoring the pet (e.g., a request to monitor the pet over a certain time period selected by the user). In some arrangements, the request may be initiated by an external computing program that has been programmed with a monitoring schedule by the user (e.g., a scheduler or calendar program associated with the user). The request may include monitoring preferences, including allowed and not allowed activities for the pet (e.g., the pet is not to enter a specified room, the pet is not to sit on the couch, etc.). The request may include alert preferences (e.g., that the user would like to receive an alert if one of the not allowed activities is detected, when a third-party should be alerted, etc.). The monitoring preferences and the alert preferences may be stored in a user account that is accessible by the base station. The user account may be stored in a database on a monitoring system server or in the monitoring system base station. Accordingly, the base station may instruct monitoring via the monitoring system according to the monitoring preferences and alert preferences associated with the user account.

After the request is received, the monitoring system is activated (804). The monitoring system may be activated from a base station. The monitoring system includes at least one monitoring device, such as monitoring devices 114 and 116 as discussed above with respect to FIG. 1. The monitoring devices may include cameras, microphones, radiofrequency receivers, speakers, location sensors, or combinations thereof (as described above with respect to monitoring devices 114 and 116). The monitoring devices are configured to gather information about a pet within a monitored area (e.g., a living area 100). The information regarding the pet may include location information, activity information, health information, and the like. The monitoring devices may be in wireless or wired communication with the base station. Accordingly, the base station may send a command directly to each monitoring device to activate each monitoring device.

Once the monitoring system is activated, the pet associated with the monitoring request is located (806). The pet may be located via a monitoring device configured to locate the pet. For example, the pet may be wearing a collar that transmits location information (e.g., derived from a GPS receiver, inertial sensors, or the like) to the base station (e.g., monitoring device 116). For example, the pet may be wearing a collar that transmits a beacon signal (e.g., using ultrasound, radiofrequency waves, or light), which is detected by one or more monitor devices 116, the data from which is used by the base station to determine (e.g., by triangulation) the pet's location. In other arrangements, a system of cameras and microphones may be able to locate the pet based on analyzing at least one of captured images and audio regarding the pet. In certain situations, a household may have multiple pets and the monitoring request may correspond to a single target pet. In such situations, the base station may be able to identify the target pet based on user programmed biometric information about the pet (e.g., pet size, fur color, audio signatures, etc.) stored within the monitoring system. The information received from the monitoring devices may be compared against the programmed biometric information to identify the target pet. The monitoring system may be able to differentiate pets from other living objects, such as humans based on detected information (e.g., image analysis, thermal image analysis, etc.). After locating the pet, the system may hone in on the pet with the monitoring devices. For example, the monitoring devices may include cameras having pan, tilt, illumination, and zoom functions, in which each of the functions may be individually adjusted to focus on the pet and/or to follow the pet based on a determined pet location (e.g., the pan and tilt functions of a monitoring device may be adjusted to keep the pet in focus as the system determines the location of the pet is moving, or the zoom and illumination may be adjusted to maintain adequate imaging quality of a moving pet). Additionally, as the pet moves from a first room or field of view to a second room or field of view (e.g., from the first bedroom 106 to the second bedroom 108), handoffs may be performed from a first monitoring device to a second monitoring device to allow for continuous monitoring of the pet even as the pet moves out of the field of view of a first monitoring device (as described above with respect to method 700).

After locating the pet, information and data regarding the pet is gathered (808). The information and data is gathered by the monitoring devices and is transmitted to the base station. In some arrangements, the gathered information and data is transmitted from the base station to a monitoring system server (e.g., system server 210). The information and data regarding the pet may include location information. The location information may relate to a detected room where the pet is present (e.g., that the pet is in the living area 104), GPS coordinates, or the like. The information and data regarding the pet may include activity information. For example, an on-pet monitor (e.g., monitoring device 116) may include a motion sensor capable of detecting the pet's acceleration, the pet's speed of movement, the pet's orientation, and the like. Alternatively or additionally, the monitoring system may be able to determine the activity information by monitoring image data captured through cameras used to track the pet (e.g., monitoring devices 114). The information and data regarding the pet may include health information. For example, an on-pet monitor (e.g., monitoring device 116) may be able to monitor a pet's heart rate, temperature, blood pressure, respiratory rate, and the like. The information and data regarding the pet may include image data. As noted above, the monitoring devices may include cameras. The cameras may capture image data concerning the pet. The image data may include still image data, video image data, thermal image data, or a combination thereof. The information and data regarding the pet may include audio data.

The gathered information and data regarding the pet is transmitted to a user device (810). The information and data is transmitted from a base station or a system server. The user device may be any one of user devices 206. The information and data transmitted to the user device may correspond to only one or more selected monitoring devices of the monitoring system. Selection may be based on range, on cameras having the pet within their field of view, on cameras offering a relatively unobstructed view of the pet, on the orientation of the pet viewed by the camera, on the image quality of the camera's view of the pet, etc.). The gathered information and data regarding the pet may be viewed by the user via the user device. The gathered information and data may be transmitted as a data stream. The data stream may be transmitted to the user device in approximately real-time as the monitoring system gathers the data and information. The base station may use the gathered information and data (e.g., the pet's physical status, determined characteristics, activity, etc.) in determining whether or not to transmit the gathered information and data (or which portion of it to transmit) to the user. For example, a user may stream video and audio data gathered from a monitoring device (e.g., monitoring device 114) to his cell phone such that the user can watch his pet while the user is away from the pet.

A request from the user to initiate a two-way communication session is received (812). In response to the request, the monitoring system may initiate a two-way communication session between the monitoring system and the user device (814). During a two-way communication session, the user may provide input into the user device, which is then transmitted over the monitoring system for output to the monitored pet through a monitoring device. For example, the user can speak a verbal message into a microphone of his cell phone during a two-way communication session (e.g., the user may say "Fido, get off the couch!"), and the monitoring system broadcasts the user's message over a monitoring device (e.g., over a speaker of monitoring device 114) such that the pet can hear the message. The user may select the target monitoring device to output the message. Alternatively, the monitoring system may automatically select the target monitoring device to output the message based on which monitoring device is closest to the pet. In some situations, the monitoring system may be connected to a television or a display within the monitored area. Accordingly, the user may be able to provide a video message to the pet via a camera of the user device. Further, the user may be able to control pan, tilt, illumination, and zoom functions of a camera of the monitoring device.

A stop request is received from the user device (816). The user may initiate the end of the two-way communication session by interacting with a user interface of the user device. In response to the stop request, the monitoring system ends the two-way communication session (818). The monitoring system may also end transmission of the data stream from the monitoring devices to the user devices.

The above systems and methods may be used to monitor multiple pets at the same time. The monitoring systems may distinguish between multiple pets based on an identifier of worn monitoring devices (e.g., monitoring device 116). In an alternative arrangement the monitoring system may analyze captured information and data regarding the multiple pets to identify each individual pet. For example, the monitoring system may analyze captured image and video data to identify each individual pet based on user programmed characteristics of each individual pet. Additionally, the monitoring system may be able to differentiate between pets and humans based on analyzing information and data captured from the monitoring devices.

It is important to note that the construction and arrangement of the elements of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the enclosure may be constructed from any of a wide variety of materials that provide sufficient strength or durability, in any of a wide variety of colors, textures, and combinations. Accordingly, all such modifications are intended to be included within the scope of the present inventions. The order or sequence of any process or method steps may be varied or re-sequenced according to alternative embodiments. Other substitutions, modifications, changes, and omissions may be made in the design, operating conditions, and arrangement of the preferred and other exemplary embodiments without departing from scope of the present disclosure or from the spirit of the appended claims.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps, and decision steps.

What is claimed is:

1. A system for monitoring a pet, comprising:
   a base station;
   a first monitoring device configured to capture first data relating to a first monitored area and to transmit the first data to the base station, wherein the first monitoring device includes a first camera and wherein the first data includes first image data; and
   a second monitoring device configured to capture second data relating to a second monitored area and to transmit the second data to the base station, wherein the second monitoring device includes a second camera and the second data includes second image data, and wherein the first monitored area and the second monitored area are adjacent to each other,
   wherein the base station is configured to
      monitor a first field of view of the first camera,
      monitor a second field of view of the second camera,
      determine a location of the pet as being in the first monitored area based at least in part on the first data and the second data,
      subsequently determine that the pet is no longer in the first field of view and is in the second field of view,
      perform a handoff from the first camera to the second camera such that the base station monitors the second field of view and no longer monitors the first field of view, and
      determine a physical status of the pet based on at least one of the first data and the second data.

2. The system of claim 1, wherein the first camera includes at least one of a pan function, a tilt function, an illumination function, and a zoom function.

3. The system of claim 2, wherein the base station is configured to adjust at least one of the pan function, the tilt function, the illumination function, and the zoom function.

4. The system of claim 3, wherein the base station is configured to adjust at least one of the pan function, the tilt function, the illumination function, and the zoom function to image the pet as the pet moves within the first monitored area.

5. The system of claim 4, wherein the base station is configured to adjust at least one of the pan function, the tilt function, the illumination function, and the zoom function to achieve a specified image quality of the pet as the pet moves within the first monitored area.

6. The system of claim 1, wherein the first monitoring device includes a first speaker.

7. The system of claim 1, further comprising a system server in communication with the base station.

8. The system of claim 7, wherein the base station is configured to transmit at least a portion of the first data or the second data to the system server.

9. The system of claim 8, wherein the base station is configured to select whether or not to transmit the portion of data based upon the determined physical status.

10. A system for monitoring a pet, comprising:
    a base station;
    a first monitoring device configured to capture first data relating to a first monitored area and to transmit the data to the base station;
    a second monitoring device configured to be carried by the pet, the second monitoring device configured to capture second data relating to the pet and to transmit the data to the base station;
    wherein the base station is configured to:
       determine a location of the pet within the first monitored area based at least in part on the second data;
       determine a physical status of the pet based on at least one of the first data and the second data;
       determine whether the physical status of the pet satisfies at least one of an automatic action condition and an alert condition;
       perform an automatic action in response to determining the physical status of the pet satisfies the automatic action condition;
       initiate an alert to a user in response to determining the physical status of the pet satisfies the alert condition; and
       perform an action in response to receiving a response to the alert from the user requesting the action.

11. The system of claim 10, wherein the first monitoring device includes a camera and wherein the first data includes to first image data.

12. The system of claim 10, wherein the first monitoring device is configured to emit ultrasonic noises.

13. The system of claim 12, wherein the ultrasonic noises are selected so as to undergo frequency conversion to specified audible noises.

14. The system of claim 10, wherein the second monitoring device includes at least one of a collar and a harness configured to be worn by the pet.

15. The system of claim 14, wherein the second monitoring device includes an odor or pheromone emitter.

16. The system of claim 10, wherein the second monitoring device includes a shocking device.

17. The system of claim 10, wherein the second monitoring device includes a biometric sensor configured to monitor a vital statistic of the pet.

18. The system of claim 17, wherein the biometric sensor includes at least one of a heartbeat monitor, a blood pressure monitor, and a thermometer.

19. The system of claim 10, wherein the second monitoring device includes a position tracking device configured to track a position of the pet.

20. The system of claim 10, wherein the second monitoring device comprises an RFID tag.

21. The system of claim 10, wherein the status of the pet includes at least one of a health characteristic of the pet or an activity of the pet.

22. A method of monitoring a pet with a pet monitoring system, the pet monitoring system including a base station and a plurality of monitoring devices in communication with the base station, the method comprising:
  receiving, at the base station, a request to monitor the pet;
  activating, by the base station, the plurality of monitoring devices;
  receiving, by the base station, data from the plurality of monitoring devices;
  determining, by the base station, a characteristic of the pet based on the data;
  determining, by the base station, whether the characteristic of the pet satisfies at least one of an automatic action condition and an alert condition;
  performing, by the base station, an automatic action in response to determining the characteristic of the pet satisfies the automatic action condition;
  initiating, by the base station, an alert to a user in response to determining the characteristic of the pet satisfies the alert condition; and
  receiving, by the base station, a response to the alert from the user, wherein the response includes a request for the pet monitoring system to perform an action.

23. The method of claim 22, wherein performing at least one of the action and the automatic action includes generating an audible alert through one of the monitoring devices.

24. The method of claim 22, wherein performing at least one of the action and the automatic action includes emitting an odor or a pheromone.

25. The method of claim 22, wherein the alert includes at least one of an e-mail, a text message, and a phone call.

26. The method of claim 22, wherein the alert includes an image of the pet captured by one of the plurality of monitoring devices.

27. The method of claim 22, wherein the characteristic includes at least one of urination, defecation, damaging an object, entering a restricted area, eating restricted food, fighting, excessive activity, sleeping, making a noise, and performing a user-specified action.

28. The method of claim 22, wherein the characteristic includes a determination that a health condition of the pet is poor.

29. The method of claim 22, wherein the plurality of monitoring devices includes a collar configured to be worn by the pet.

30. The method of claim 29, wherein performing at least one of the action and the automatic action includes shocking the pet through a shocking device on the collar.

* * * * *